United States Patent
Fix et al.

(10) Patent No.: US 9,465,004 B2
(45) Date of Patent: Oct. 11, 2016

(54) SENSOR DEVICE FOR SENSING A GAS, METHOD FOR OPERATING A SENSOR DEVICE FOR SENSING A GAS AND PRODUCTION METHOD FOR A SENSOR DEVICE FOR SENSING A GAS

(71) Applicant: Robert Bosch GmbH, Stuttgart (DE)

(72) Inventors: Richard Fix, Gerlingen (DE); Denis Kunz, Untergruppenbach (DE); Andreas Krauss, Tuebingen (DE); Kathy Sahner, Leonberg (DE); Philipp Nolte, Gerlingen (DE)

(73) Assignee: Robert Bosch GmbH, Stuttgart (DE)

( * ) Notice: Subject to any disclaimer, the term of this patent is extended or adjusted under 35 U.S.C. 154(b) by 197 days.

(21) Appl. No.: 14/217,561

(22) Filed: Mar. 18, 2014

(65) Prior Publication Data

US 2014/0283581 A1    Sep. 25, 2014

(30) Foreign Application Priority Data

Mar. 19, 2013 (DE) .................... 10 2013 204 811

(51) Int. Cl.
- *G01N 7/00* (2006.01)
- *G01N 9/00* (2006.01)
- *G01N 27/407* (2006.01)

(52) U.S. Cl.
CPC .................. *G01N 27/407* (2013.01)

(58) Field of Classification Search
None
See application file for complete search history.

(56) References Cited

U.S. PATENT DOCUMENTS

| | | | | |
|---|---|---|---|---|
| 5,841,021 A | * | 11/1998 | De Castro | G01N 27/4162 204/424 |
| 7,279,080 B2 | * | 10/2007 | Chapples | G01N 27/4074 204/424 |
| 7,416,650 B2 | * | 8/2008 | Hatada | G01N 27/4074 204/406 |
| 7,671,600 B2 | * | 3/2010 | Suzuki | G01N 27/407 324/465 |
| 8,016,988 B2 | * | 9/2011 | Chou | G01N 27/407 204/424 |

FOREIGN PATENT DOCUMENTS

| | | |
|---|---|---|
| DE | 102 47 857 A1 | 4/2004 |
| DE | 10 2007 021 913 A1 | 11/2008 |

OTHER PUBLICATIONS

Machine translation of DE 102007021913.*

* cited by examiner

*Primary Examiner* — Michael A Lyons
*Assistant Examiner* — Jermaine Jenkins
(74) *Attorney, Agent, or Firm* — Maginot, Moore & Beck LLP

(57) ABSTRACT

A sensor device for sensing a gas includes a sensing region, and a readout region that is electrically and mechanically connected to the sensing region by way of a connecting web. The readout region, the sensing region, and the connecting web are formed from a substrate, and are isolated from the substrate by a clearance cutout. The sensing region has an ion-conducting region configured to provide a measuring signal dependent on the gas. The readout region (is configured to read out the measuring signal.

14 Claims, 2 Drawing Sheets

SENSOR DEVICE FOR SENSING A GAS, METHOD FOR OPERATING A SENSOR DEVICE FOR SENSING A GAS AND PRODUCTION METHOD FOR A SENSOR DEVICE FOR SENSING A GAS

This application claims priority under 35 U.S.C. §119 to patent application no. DE 10 2013 204 811.4, filed on Mar. 19, 2013 in Germany, the disclosure of which is incorporated herein by reference in its entirety.

BACKGROUND

The present disclosure relates to a sensor device for sensing a gas, a method for operating such a sensor device and a production method for producing such a sensor device.

For some years, research activities concerning miniaturization of the high-temperature fuel cell (SOFC, solid oxide fuel cell) have been conducted. The aim of this is to combine ion-conducting ceramic materials from conventional SOFC technology and microfabrication steps from semiconductor process technology and present a micro-SOFC. In parallel with these research activities, an increasing miniaturization of ceramic exhaust gas sensors is also taking place. The base material for both applications is an oxygen-ion-conducting ceramic (usually yttrium-stabilized zirconia, YSZ); Pt comes into consideration for example as the electrode material.

DE 102 47 857 A1 discloses a gas sensor obtained by ceramic multilayer technology. The gas sensor comprises a hot plate for gas detection, which is fastened to one or more narrow arms monolithically connected to the hot plate, the hot plate and the arms being at least partially configured by ceramic multilayer technology.

SUMMARY

Against this background, a sensor device for sensing a gas, a method for operating a sensor device for sensing a gas and a production method for a sensor device for sensing a gas are presented by the present disclosure. Advantageous configurations are provided by the claims and the description that follows.

With an arrangement of a sensing region of small dimensions of a gas sensor in a clearance of a semiconductor substrate, forming the gas sensor, surrounded by a readout region of the gas sensor, an ionic-conductor-based sensing can be realized for low-temperature applications.

According to the concept presented here, it is possible by methods of microsystems technology to miniaturize the sensitive region or sensing region of the ionic-conductor-based sensor in such a way as to achieve a thermal capacity of the sensitive region that is as low as possible and at the same time attain a thermal detachment from the surrounding chip periphery that is as great as possible.

According to the approach that is presented here, the sensitive region, which may for example comprise an ion-conducting thin film with one or more electrodes and may possibly be heated to obtain an adequate sensor function, represents only a partial region of the sensor chip or of the sensor device. Consequently, a very significant advantage of the disclosure is that, with the low thermal capacity of the sensitive region that is achieved, operation of the sensor with very brief temperature peaks is also possible, with the result that an average overall sensor temperature can remain much lower than the brief peak temperature of the sensitive region. Therefore, at very high temperatures, a measured value can be recorded in a short time without much power being required and without macroscopic heating of the surroundings of the sensitive region taking place.

Altogether, the approach proposed here makes it possible to use ionic-conductor-based sensors in sensor applications in which the sensor chip is only allowed to require negligible energy or to generate negligible operational heat, which is indispensable for use in fire alarms or cellular phones. In addition, very low-cost sensors can be realized by the miniaturization concept proposed here, and a high selectivity of the sensors can be achieved by the selective ion conductivity.

For example, the approach proposed here is recommendable for the design of gas sensors in connection with the lambda probe of a vehicle. The fact that much higher temperatures than room temperature are usually required for an adequate function both of the electrode and of the ionic conductor is important in this connection. For example, heating to 600 to 700° C. is usual in the case of lambda probes. An approach to miniaturization using semiconductor process technology has in fact already been described for the lambda probe too, and a lowering by several hundreds of degrees is possible by improving the qualities of the materials. However, an adequate function of the materials at room temperature continues to appear to be very unlikely. With the concept proposed here, this set of problems can be solved, since the heating power requirement is much lower, and so the measuring principle proposed here also comes into consideration for applications in which the entire macroscopic sensor unit must not be at a temperature much higher than room temperature.

A sensor device for sensing a gas comprises a sensing region and a readout region that is electrically and mechanically connected to the sensing region by way of a connecting web, the readout region, the sensing region and the connecting web being formed from a substrate and the sensing region and the connecting web being isolated from the substrate by cutting out a clearance, the sensing region having an ion-conducting region for providing a measuring signal dependent on the gas and the readout region being designed for the reading out of the measuring signal.

The sensor device may for example be used as a lambda probe or in connection with a lambda probe in a vehicle, in order to determine the composition of an exhaust gas mixture of the vehicle. For sensing the gas, the sensor device may be arranged in or close to a stream of the gas. The substrate forming the sensor device may for example be a semiconductor substrate or a glass substrate. For example, the substrate may consist of silicon or comprise silicon. The substrate may have an outer extent of a cuboid or a small plate. The sensing region of the sensor device may be designed for the detection of one or more constituents of the gas. The sensing region may be designed to provide the measuring signal for example depending on a presence or absence of the gas or on a concentration of the gas. The measuring signal may be an electric current or an electric voltage. The ion-conducting region may form an ionic conductor. The ion-conducting region may for example be formed as a solid-state electrolyte. In particular, the ion-conducting region may have an electrode that can be used for building up an electric field and for heating the sensing region. The ion-conducting region, which may also be referred to as a sensitive region, may be distinguished by the fact that it is produced by microsystems technology and merely makes up a small fraction of an overall volume of the sensor device. The sensing region may be arranged in a central portion of the sensor device. Physical depositing processes, such as for example sputtering or laser ablation, or chemical depositing processes, in particular chemical vapor deposition and atomic layer deposition, may be used as production methods for an ion-conducting region. The readout region may be arranged around the sensing region or be arranged adjoining the connecting web. The readout region may be designed to receive the measuring signal by way of the connecting web. The readout region may be designed to pass on the measuring signal to an evaluation circuit. Alternatively, the readout region may be designed to determine on the basis of the measuring signal information concerning a quality and/or composition of the gas. For example, the readout region may have an evaluation circuit for evaluating the measuring signal and for providing measurement data based on the measuring signal. The readout region may for example have a transistor circuit for the evaluation of the measuring signal or be formed by a corresponding integrated circuit. Such an integrated circuit can be incorporated in the substrate by processing using methods of semiconductor technology. The clearance may for example be arranged centrally on the substrate and be formed as a clearance or a through-hole through the substrate. A free space formed by the clearance may have greater dimensions than the sensing region. The sensing region may be arranged in the clearance in such a way that it is for example uniformly spaced from walls of the semiconductor substrate that bound the clearance, and consequently there is an air gap between the sensing region and the readout region. The connecting web may be designed to bridge the gap, and consequently to perform a function of a carrier structure for the sensing region and at the same time a function of coupling the sensing region to the readout region.

According to one embodiment of the sensor device, a thermal conductivity of the sensing region may be greater than a thermal conductivity of the connecting web and/or of the readout region. Thus, only the region of the sensor device that is intended for recording the measured variable may be exposed to an increased temperature required for the recording of the measured variable, while the remaining regions of the sensor device can remain at a lower temperature level. The differing thermal conductivity may be realized for example by a suitable choice of materials. In this way, a lifetime of the sensor device can be advantageously extended and its use in devices that would be functionally adversely affected by a temperature increase can be made possible.

For example, the readout region may comprise a circuit which is integrated in the substrate. In this way, an evaluation of the measuring signal provided by the sensing region can be performed in minimal installation space.

Alternatively or in addition, the readout region may comprise at least one terminal for passing on the measuring signal to an evaluation circuit, the evaluation circuit being designed to evaluate the measuring signal provided by the sensing region. The evaluation circuit may be formed as a circuit arranged on a separate substrate. The evaluation circuit may represent an integrated circuit, known as a chip. The evaluation circuit may for example be mounted on the readout region and be connected to the terminal of the readout region by way of a line, for example a bonding wire or a soldered connection. The readout region and the evaluation circuit may be surrounded by a common housing.

The sensor device may be configured as a microsystems technology element. Consequently, processes of microsystems technology can be used to produce structures of the sensor device. Processes of semiconductor technology may also be used for this. For example, the ion-conducting region may be produced using processes of microsystems technology. A structural resolution of functional structures of the sensor device may lie in the range of micrometers or less.

According to one embodiment, the connecting web may have at least one electrical line for the electrical coupling of the sensing region to the readout region. For example, the at least one electrical line may be embedded in the connecting web and/or be completely surrounded by it. Thus, a space-saving and short-circuit-proof electrical connection can be established between the sensing region and the readout region.

For example, the sensor device may have a further ion-conducting region for providing a further measuring signal dependent on the gas and the readout region may be designed for the reading out of the further measuring signal. In this case, the ion-conducting regions may comprise different ion-conducting materials. For example, the ion-conducting regions may be produced using different electrode materials. It can thus be ensured in a simple and low-cost way that the sensor device can be used for the investigation of different gases.

Furthermore, the sensor device may have a further connecting web. Correspondingly, the connecting web may connect a side face of the sensing region that is facing the readout region to a side face of the readout region that forms the clearance, and the further connecting web may connect a further side face of the sensing region that is facing the readout region and is opposite from the first-mentioned side face of the sensing region to a further side face of the readout region that forms the clearance and is opposite from the first-mentioned side face of the readout region. This embodiment has the advantage that the sensing region can be anchored in the sensor device in a particularly robust manner and, moreover, a galvanic separation of the electrical lines for the coupling of the sensing region and the readout region is dependably ensured.

A method for operating a sensor device according to one of the embodiments explained above has the following steps:

heating the sensing region; and reading out a measured value, representing the measuring signal, from the readout region of the sensor device.

The heating step may be carried out for example by electrodes arranged in the sensing region. The reading-out step may be carried out for example when, as a result of the heating, the sensing region has reached a temperature that brings about an ion flow in the sensing region, on the basis of which a measured variable to be sensed or measured variables to be sensed can be detected in the gas stream. The method for operating the sensor device may for example be controlled in an open-loop or closed-loop manner by means of a control device coupled to the sensor device.

According to one embodiment of the method, the heating step may be carried out for a short time within an operating time of the sensor device. The heating step may have a duration of a fraction of an operating time of the sensor device. The duration may in this case be less than or equal to 10 seconds. Thus, the sensing region may be only briefly heated for recording the measured value, in order to allow it subsequently to cool down again immediately. In this way, the lifetime and energy efficiency of the sensor device can be advantageously extended or improved.

Furthermore, in the heating step, the sensing region may be heated at successive times to a first temperature level and to a second temperature level. Correspondingly, in the reading-out step, the measured value during a period at the first temperature level may be read out and a further measured value during a period at the second temperature level may be read out. With this embodiment, for example, different substances in a gas mixture can be readily determined by the sensor device.

A production method for a sensor device for sensing a gas has the following steps:

providing a substrate, with a sensing region for carrying an ion-conducting region for providing a measuring signal dependent on the gas, a readout region for reading out the measuring signal and a connecting web for electrically and mechanically connecting the sensing region to the readout region; and producing a clearance from the substrate, in order to isolate the sensing region and the connecting web from the substrate.

The step of producing the clearance may be carried out for example by machine by means of an etching process.

The production method may comprise a step of applying the ion-conducting region to the sensing region, at a time after the step of producing the clearance. Alternatively, the sensing region may already comprise the ion-conducting region before the sensing region is isolated.

The present disclosure also provides a control device, which is designed to carry out or implement the steps of the method for operating a sensor device in connection with units of the control device. The object on which the disclosure is based can also be quickly and efficiently achieved by this configurational variant of the disclosure in the form of a control device.

BRIEF DESCRIPTION OF THE DRAWINGS

The disclosure is explained in more detail below by way of example on the basis of the accompanying drawings, in which.

DETAILED DESCRIPTION

In the description that follows of preferred exemplary embodiments of the present disclosure, the same or similar reference signs are used for the elements that are represented in the various figures and act in a similar way, without the description of these elements being repeated.

Figure 1A:
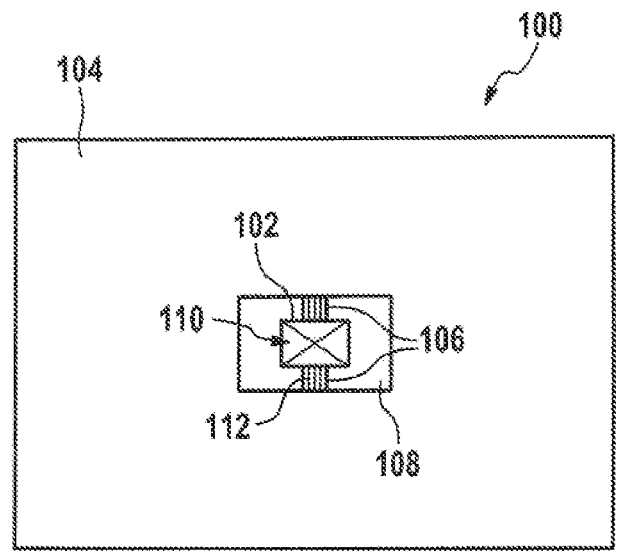
FIG. 1A shows a plan view of a sensor device for sensing a gas according to an exemplary embodiment of the present disclosure.

FIG. 1A shows in a plan view a schematic representation of a sensor device 100 for sensing a gas according to an exemplary embodiment of the disclosure. The sensor device 100 is cuboidal and is made up of a sensing region 102, a readout region 104 and two connecting webs 106. The sensor device 100 consists entirely of a substrate, for example a semiconductor substrate, and is given the specific form that is shown in the representation in an etching process. The sensing region or sensitive region 102 and also the connecting webs 106 are isolated from the substrate by cutting out a clearance 108, formed in the etching process. The connecting webs 106 connect the sensing region 102 on opposite sides to the readout region 104, and thereby form a mechanical suspension of the sensitive region 102 arranged in the cut-out region 108. In addition, the connecting webs 106 establish an electrical connection between the sensing region 102 and the readout region 104 by way of electrical lines or leads 112 arranged in or on them. The readout region 104 has an integrated circuit and is consequently also referred to as a sensor chip.

For sensing a gas, the sensor device 100 may be arranged in a gas stream. The sensing region or sensitive region 102 is formed as an ionic conductor and has one or more electrodes and also a heating element 110, and can consequently be heated up to a required operating temperature for sensing a measured variable from the gas stream. A measured variable sensed from the gas stream is transmitted as a measuring signal by way of the lines 112 to the readout region 104 and is evaluated there. The schematic representation in FIG. 1A illustrates that the sensing region 102, produced by microsystems technology, is made much smaller than the readout region 104 of the sensor device 100, whereby the advantageous low thermal capacity of the sensor device 100 can be achieved. The clearance 108 also assists rapid cooling down of the sensitive region, for example after recording the measured value.

For sensing the gas, according to an exemplary embodiment a first portion of the sensing region 102 may be brought into contact with the gas to be sensed and a second portion of the sensing region, arranged spatially separated from the first portion by the ionic conductor, may be brought into contact with a reference gas. The measuring signal may be generated by ions that pass through the ionic conductor between the first portion and the second portion. The ionic conductor may be configured as a membrane, which may be arranged between two electrodes lying opposite one another for picking off the measuring signal.

As the representation in FIG. 1 shows, the sensitive region 102 with the ionic conductor is isolated from the readout region 104, forming the main region of the substrate, by means of the cut-out 108, produced by etching processes. The sensing region 102 is mechanically and electrically connected, for example by means of the metallic conductor tracks 112 or implanted, doped regions, to the rest of the substrate through the connecting webs or suspensions 106, which are preferably formed from a material with low thermal conductivity. The temperature of the sensitive region 102 may be sensed for example by the resistance of the heating element 110 or by the impedance of the ionic conductor or an additionally integrated temperature measuring element. The readout region 104 is formed here by an Si-based chip.

Figure 1B:
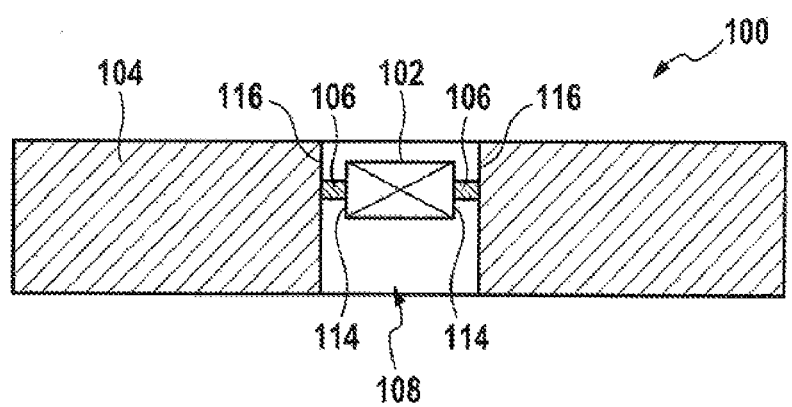
FIG. 1B shows a cross section through the sensor device for sensing a gas from FIG. 1A.

FIG. 1B shows the sensor device 100 for sensing a gas on the basis of a schematic cross-sectional representation according to an exemplary embodiment of the present disclosure. This form of representation graphically shows that an overall height of the readout region 104 is greater than an overall height of the sensing region 102, and an overall height of the sensing region 102 is greater than an overall height of the connecting webs 106. With this specific form of the sensor device 100, the advantageous low thermal capacity of the sensing region 102 can be optimally produced, since the clearance 108 that is formed by means of the etching process in the production method offers sufficient volume for the isolation of the sensing region 102 and, as a result of the miniaturization of the sensing region 102, it can be heated particularly quickly and also for a short time. In the case of the exemplary embodiment shown here of the sensor device 100, the connecting webs 106 are formed and arranged by the etching process in such a way that each connecting web 106 connects a side face 114 of the sensing region 102 that is facing the readout region 104 to a side face 116 of the readout region 104 that forms the clearance 108.

In an advantageous enhancement of the sensor device 100 for sensing a gas that is shown in FIGS. 1A and 1B, it is possible for example to use a number of sensitive regions 102 on a chip or semiconductor substrate with different electrode materials, in order to measure a number of gases at the same time. A cycling of the measured value acquisition over a number of temperature levels is similarly conceivable, in order to use temperature dependencies of the sensitive properties for more sensor information, for example in terms of selectivity, sensing a number of gases, different calibrations, etc.

Any desired exemplary embodiment of the ionic-conductor-based sensor device 100 that is explained on the basis of FIGS. 1A and 1B is in any case designed such that it is also possible for it to be used in applications that do not allow a high sensor temperature and/or high power consumption.

The representations in FIGS. 1A and 1B for the basic construction of the sensor device 100 are schematic and not to scale.

Figure 2:
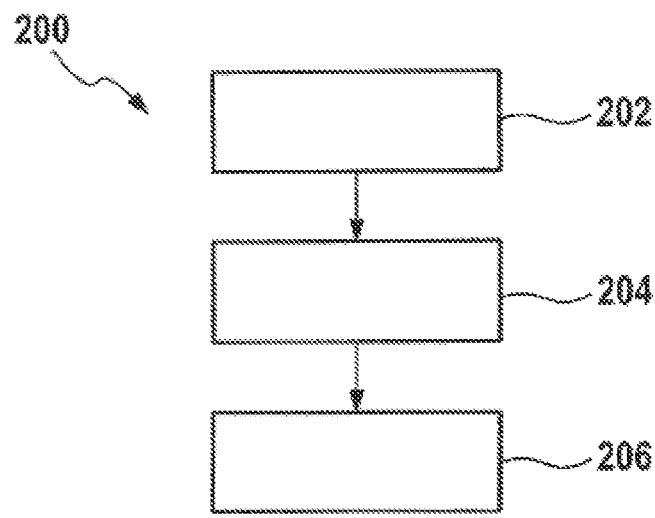
FIG. 2 shows a flow diagram of a method for operating a sensor device for sensing a gas according to an exemplary embodiment of the present disclosure.

FIG. 2 shows an exemplary embodiment of a flow diagram of a method 200 for operating a sensor device for sensing a gas. In a step 202, a sensing region or sensitive region of the sensor device is heated. A measured value or a measured variable is sensed from a gas flowing through the sensor device in a step 204. In a step 206, the measured value sensed in step 204 is evaluated in a readout region of the sensor device.

The reading out and evaluating of the ionic conductor to be carried out in step 206 may be performed in particular on the basis of the Nernst potential produced and/or on the basis of the ion current flowing with a known voltage.

Steps 202 and 204 of the method 200 may be carried out in the units of the sensor device explained on the basis of FIGS. 1A and 1B.

In a preferred configurational variant of the method 200, for dynamic operation of the sensor device, in the heating step 202 an electric voltage for heating the sensing region is applied, with the power necessary for reaching a minimum measuring temperature, for less than 100% of the operating time. In a further advantageous configurational variant, in the heating step 202 the heating power is applied only for 1% of the overall operating time and the sensor signal is evaluated after reaching the measuring temperature of the sensitive region required as a minimum. Subsequently, the sensitive region cools down again immediately and the sensor is switched off for the remaining 99% of the operating time. Thus, in total, only 1% of the heat output that would otherwise be required in constant operation is dissipated.

Figure 3:
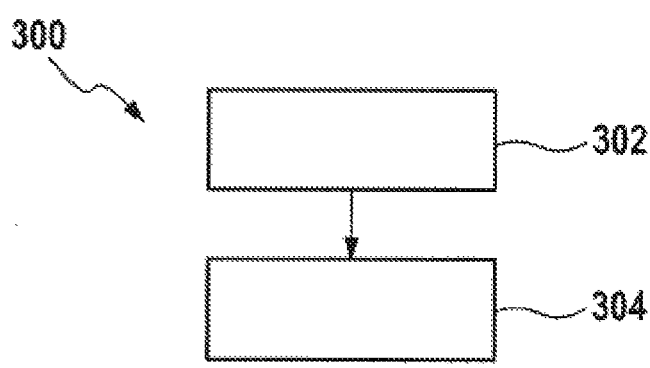
FIG. 3 shows a flow diagram of a method for producing a sensor device according to an exemplary embodiment of the present disclosure.

FIG. 3 shows an exemplary embodiment of a flow diagram of a method 300 for producing a sensor device for sensing a gas, such as that shown for example in FIG. 1.

In a step 302, a substrate is provided, incorporating a sensing region formed as an ionic conductor, a readout region and a connecting web for the electrical and mechanical connection of the sensing region to the readout region. In a step 304, the sensing region and the connecting web are isolated from the semiconductor substrate.

According to an alternative exemplary embodiment, in step 302 a substrate which in particular does not yet incorporate the ion-conducting region may be provided. According to this exemplary embodiment, the ion-conducting region and possibly further functional regions of the sensor device, such as for example conducting connections of the connecting web, may be incorporated by processing in a further step, which is carried out after the isolating step 304.

If no evaluation circuit for evaluating the measuring signal is integrated in the readout region, the readout region may be connected to a suitable evaluation circuit in a further step, which may be carried out for example likewise at a time after step 304. For example, an element comprising the evaluation circuit, for example a chip, may be mounted on the substrate.

A use of the ionic-conductor-based sensor that is explained and described on the basis of the figures above for low-temperature applications is conceivable in motor-vehicle and non-motor-vehicle applications, for example as a mobile and stationary lambda probe or as an O2, NOx, HC or NH3 sensor. Other suitable uses are for example in power saws, baking ovens, refrigerators, cellular phones, microwaves, sports watches, toasters, fire alarms and in medical technology or in a breathalyzer.

The exemplary embodiments described and shown in the figures are chosen merely by way of example. Different exemplary embodiments may be combined with one another completely or with respect to individual features. One exemplary embodiment may also be supplemented by features of another exemplary embodiment. Furthermore, method steps according to the disclosure may be repeated and carried out in a sequence other than that described.

What is claimed is:

1. A sensor device for sensing a gas, comprising:
   a sensing region that includes an ion-conducting region configured to provide a measuring signal based at least in part upon the gas; and
   a readout region electrically and mechanically connected to the sensing region via a connecting web, and configured to read out the measuring signal;
   wherein the sensing region, the readout region, and the connecting web are formed from a substrate; and
   wherein the sensing region, the readout region, and the connecting web are isolated by a clearance.

2. The sensor device according to claim 1, wherein a thermal conductivity of the sensing region is greater than a thermal conductivity of at least one of the connecting web and the readout region.

3. The sensor device according to claim 1, wherein the readout region includes a circuit that is integrated into the substrate and configured to evaluate the measuring signal.

4. The sensor device according to claim 1, wherein:
   the readout region includes at least one terminal configured to pass the measuring signal to an evaluation circuit; and
   the evaluation circuit is configured to evaluate the measuring signal.

5. The sensor device according to claim 1, further configured as a microsystems technology element.

6. The sensor device according to claim 1, wherein the connecting web includes at least one electrical line configured to electrically couple the sensing region to the readout region.

7. The sensor device according to claim 1, wherein:
   the sensing region includes a further ion-conducting region configured to provide a further measuring signal based at least in part upon the gas
   the further ion-conducting region has different ion-conducting materials than ion conducting materials of the ion-conducting region; and
   the readout region is further configured to read out the further measuring signal.

8. The sensor device according to claim 1, further comprising a further connecting web, wherein:
the connecting web connects a side face of the sensing region that is facing the readout region to a side face of the readout region that forms the clearance; and
the further connecting web connects a further side face of the sensing region that is facing the readout region and is opposite from the side face of the sensing region to a further side face of the readout region that forms the clearance and is opposite to the side face of the readout region.

9. A method of using a sensor device, comprising:
heating a sensing region of the sensor device that includes an ion-conducting region configured to provide a measuring signal based at least in part upon a gas; and
reading out a measured value representative of a measuring signal from a readout region of the sensor device that is electrically and mechanically connected to the sensing region via a connecting web, and configured to read out the measuring signal;
wherein the sensing region, the readout region, and the connecting web are formed from a substrate; and
wherein the sensing region, the readout region, and the connecting web are isolated by a clearance.

10. The method of using a sensor device according to claim 9, wherein the heating is performed within an operating time of the sensor device.

11. The method of using a sensor device according to claim 9, wherein:
heating the sensing region includes successively heating the sensing region to a first temperature and to a second temperature; and
reading out the measured value includes:
reading out the measured value during a first period when the sensing region is heated to the first temperature; and
reading out the measured value during a second period when the sensing region is heated to the second temperature.

12. A method of producing a sensor device for sensing a gas, comprising:
forming, using a substrate:
a sensing region configured to carry an ion-conducting region that provides a measuring signal based at least in part upon the gas;
a readout region configured to read out the measuring signal; and
a connecting web that electrically and mechanically connects the sensing region to the readout region; and
producing a clearance from the substrate that isolates the sensing region and the connecting web from the substrate.

13. The method of producing a sensor device according to claim 12, wherein producing the clearance includes an etching process.

14. The method of producing a sensor device according to claim 12, further comprising applying the ion-conducting region to the sensing region after producing the clearance.

* * * * *